United States Patent
Koeda et al.

Patent Number: 6,007,485
Date of Patent: Dec. 28, 1999

[54] PORTABLE ENDOSCOPE

[75] Inventors: Takashi Koeda, Tokyo; Hiroshi Sano, Chiba; Kunitoshi Ikeda, Tokyo; Hirohisa Ueda, Saitama; Kunikiyo Kaneko; Rensuke Adachi, both of Tokyo, all of Japan

[73] Assignee: Asahi Kogaku Kogyo Kabushiki Kaisha, Tokyo, Japan

[21] Appl. No.: 09/143,646

[22] Filed: Aug. 31, 1998

[30] Foreign Application Priority Data

Sep. 11, 1997 [JP] Japan ................................ 9-246267

[51] Int. Cl.$^6$ ........................................ A61B 1/06
[52] U.S. Cl. ............................ 600/178; 600/179
[58] Field of Search ................................ 600/132, 160, 600/178, 179, 180, 199, 200, 248, 249

[56] References Cited

U.S. PATENT DOCUMENTS

| | | | |
|---|---|---|---|
| 2,102,274 | 12/1937 | Larimore | 600/178 |
| 2,235,979 | 3/1941 | Brown | 600/178 |
| 2,236,842 | 4/1941 | Allyn | 600/178 |
| 3,066,569 | 12/1962 | MacDonald | 600/178 |
| 3,592,199 | 7/1971 | Ostensen | 600/199 |
| 3,766,909 | 10/1973 | Ozbey | 600/193 |
| 4,402,313 | 9/1983 | Yabe | 600/178 |
| 4,483,585 | 11/1984 | Takami | 600/178 |
| 4,580,198 | 4/1986 | Zinnanti | 600/178 |
| 4,583,528 | 4/1986 | Bauman | 600/178 |
| 4,823,244 | 4/1989 | Alaybayoglu et al. | 600/178 |
| 5,097,399 | 3/1992 | Gammache | 362/197 |
| 5,170,775 | 12/1992 | Tagami | 600/178 |
| 5,394,865 | 3/1995 | Salerno | 600/199 |
| 5,542,904 | 8/1996 | Heine | 600/199 |
| 5,588,950 | 12/1996 | Sano et al. | . |
| 5,717,807 | 2/1998 | Thereoux | 600/178 |
| 5,735,794 | 4/1998 | Koeda et al. | . |
| 5,743,848 | 4/1998 | Koeda et al. | . |
| 5,746,494 | 5/1998 | Koeda et al. | . |
| 5,800,343 | 9/1998 | Takeuchi | 600/178 |

*Primary Examiner*—John P. Leubecker
*Attorney, Agent, or Firm*—Greenblum & Bernstein, P.L.C.

[57] ABSTRACT

A portable endoscope having a light guide for transmitting light to illuminate an object. The light guide has an entrance end portion disposed in a control part. An illuminating light supply unit contains a power supply for supplying the illuminating light to the light guide. The illuminating light supply unit is detachably connected to the control part. A lamp serving as a light source of the illuminating light is provided such that when the illuminating light supply unit is detached from the control part, the lamp is left in the control part.

12 Claims, 6 Drawing Sheets

PORTABLE ENDOSCOPE

BACKGROUND OF THE INVENTION

The present disclosure relates to subject matter contained in Japanese Patent Application No. 9-246267 (filed on Sept. 11, 1997), which is expressly incorporated herein by reference in its entirety.

1. Field of the Invention

The present invention relates to a portable endoscope in which an illuminating light supply unit for supplying illuminating light to a light guide is detachably connected to a control part of the endoscope.

2. Description of the Prior Art

In portable endoscopes having a light-emitting member for illumination provided in an endoscope control part, an entrance end portion of a light guide for transmitting light to illuminate an object is generally disposed in the control part, and an illuminating light supply unit is detachably connected to the control part. The illuminating light supply unit contains a light source lamp for supplying illuminating light to the light guide. The illuminating light supply unit further contains a battery or the like that serves as a power supply for the light source lamp.

When the illuminating light supply unit is not connected to the control part, the light source lamp need not be turned on. However, if the doctor forgets to switch off the light source lamp in the illuminating light supply unit as detached from the control part, it takes a long time for the doctor to become aware of the fact in many cases because the endoscope is not used. Consequently, the power supply battery is consumed uselessly.

The occurrence of such a problem can be prevented by providing, in addition to the hand-operated switch, a switch that performs a switching operation in response to attaching and detaching the illuminating light supply unit to and from the control part. This is, however, undesirable because provision of such a switch causes the structure to become complicated and large in size.

SUMMARY OF THE INVENTION

An object of the present invention is to provide a portable endoscope designed so that when the illuminating light supply unit is detached from the control part, the light source lamp is surely turned off without the need to provide a switch that operates in response to attaching and detaching the illuminating light supply unit with respect to the control part, thereby enabling prevention of useless consumption of the power supply.

Other objects and advantages of the present invention will become apparent from the following detailed description of an illustrated embodiment of the invention.

According to the present invention, there is provided a portable endoscope having a light guide for transmitting illuminating light to illuminate an object. The light guide has an entrance end portion disposed in a control part of the endoscope. The portable endoscope further has an illuminating light supply unit containing a power supply for supplying the illuminating light to the light guide. The illuminating light supply unit is detachably connected to the control part. The portable endoscope includes a lamp serving as a light source of the illuminating light. The lamp is provided such that when the illuminating light supply unit is detached from the control part, the lamp is left in the control part.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

An embodiment of the present invention will be described below with reference to the accompanying drawings.

Figure 1:
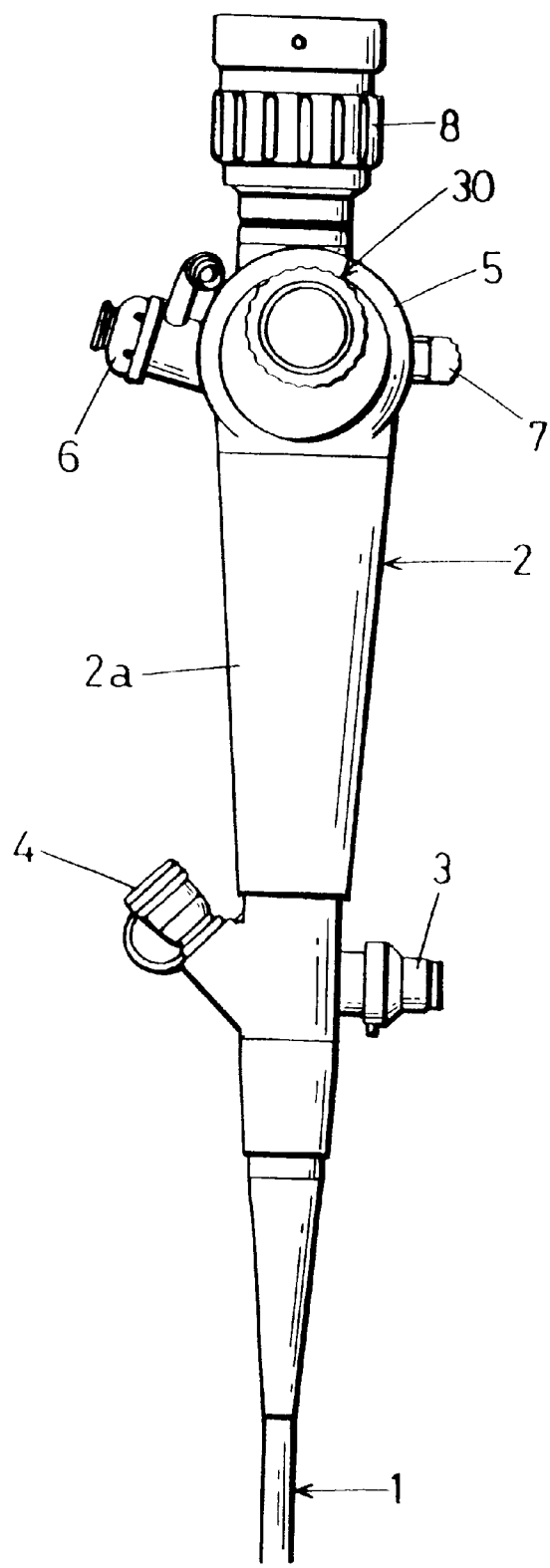
FIG. 1 is a side view of a portable endoscope according to an embodiment of the present invention.
Figure 2:
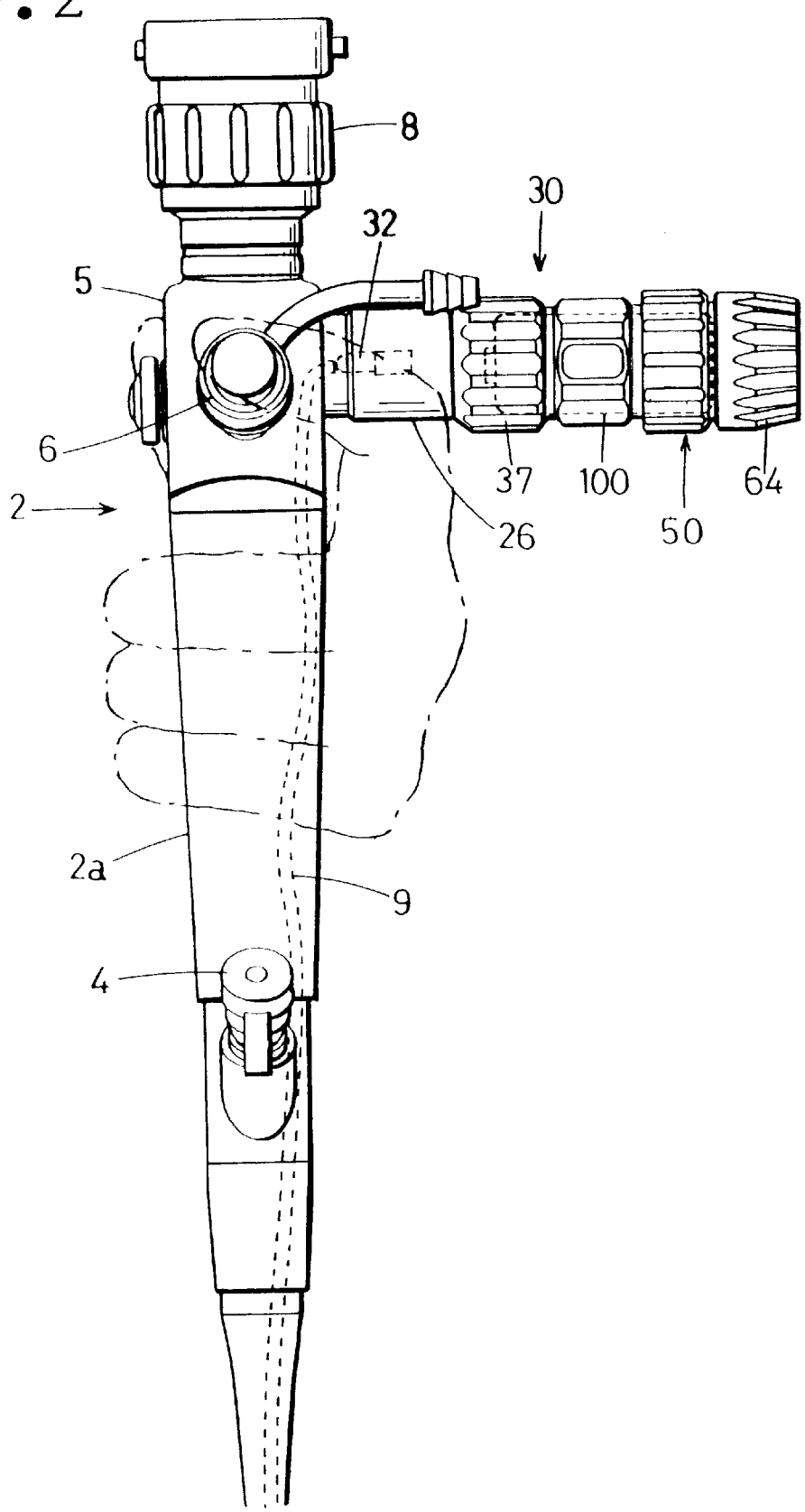
FIG. 2 is a front view of the portable endoscope according to the embodiment of the present invention.

FIG. 1 is a side view of a portable endoscope according to an embodiment of the present invention, showing a control part 2 and other constituent parts of the endoscope. FIG. 2 is a front view of the endoscope. A proximal end of an insert part 1 is connected to the lower end of the control part 2. The insert part 1 is covered with a flexible tube.

About three-fourths from the bottom of the control part 2 is a grip portion 2a. A forceps inlet 4 is provided between the grip portion 2a and the insert part 1 so as to project obliquely forward. A pressure control valve 3 is used to control the pressure in the endoscope, which is formed into an airtight structure.

The control part 2 has a control mechanism portion 5 above the grip portion 2a. The control mechanism portion 5 has a suction control valve 6 that is disposed on the front side thereof to carry out a suction operation through a forceps channel (not shown) inserted in the insert part 1. The control mechanism portion 5 further has a bending control lever 7 that is disposed on the rear side thereof to effect bending control of a remote-controlled bendable portion (not shown) that is formed at the distal end of the insert part 1. In addition, an eyepiece 8 is provided on the top of the control mechanism portion 5.

A light guide fiber bundle 9 for transmitting light to illuminate an object has an entrance end portion disposed in the control mechanism portion 5. The light guide fiber bundle 9 extends through the insert part 1 and the grip portion 2a of the control part 2. The exit end portion of the light guide fiber bundle 9 is disposed in the distal end of the insert part 1.

An illuminating light supply unit 30 for supplying illuminating light to the light guide fiber bundle 9 is detachably connected to a side of the control mechanism portion 5 to project sideways.

A light source lamp 32, shown by the dashed line in FIG. 2, emits illuminating light to be supplied to the light guide fiber bundle 9. The illuminating light supply unit 30 contains a battery 100 as a power supply for lighting the light source lamp 32. The battery 100 may be any type of battery, e.g. a dry battery or a rechargeable nickel-cadmium battery.

The battery 100 can be replaced by removing a cap 50 that is detachably attached to the outer end of the illuminating light supply unit 30. An AC/DC conversion adapter or the like may be connected to the illuminating light supply unit 30 in place of the battery 100. A switch control ring 64 is used to switch on/off the light source lamp 32 by a manual operation.

Figure 3:
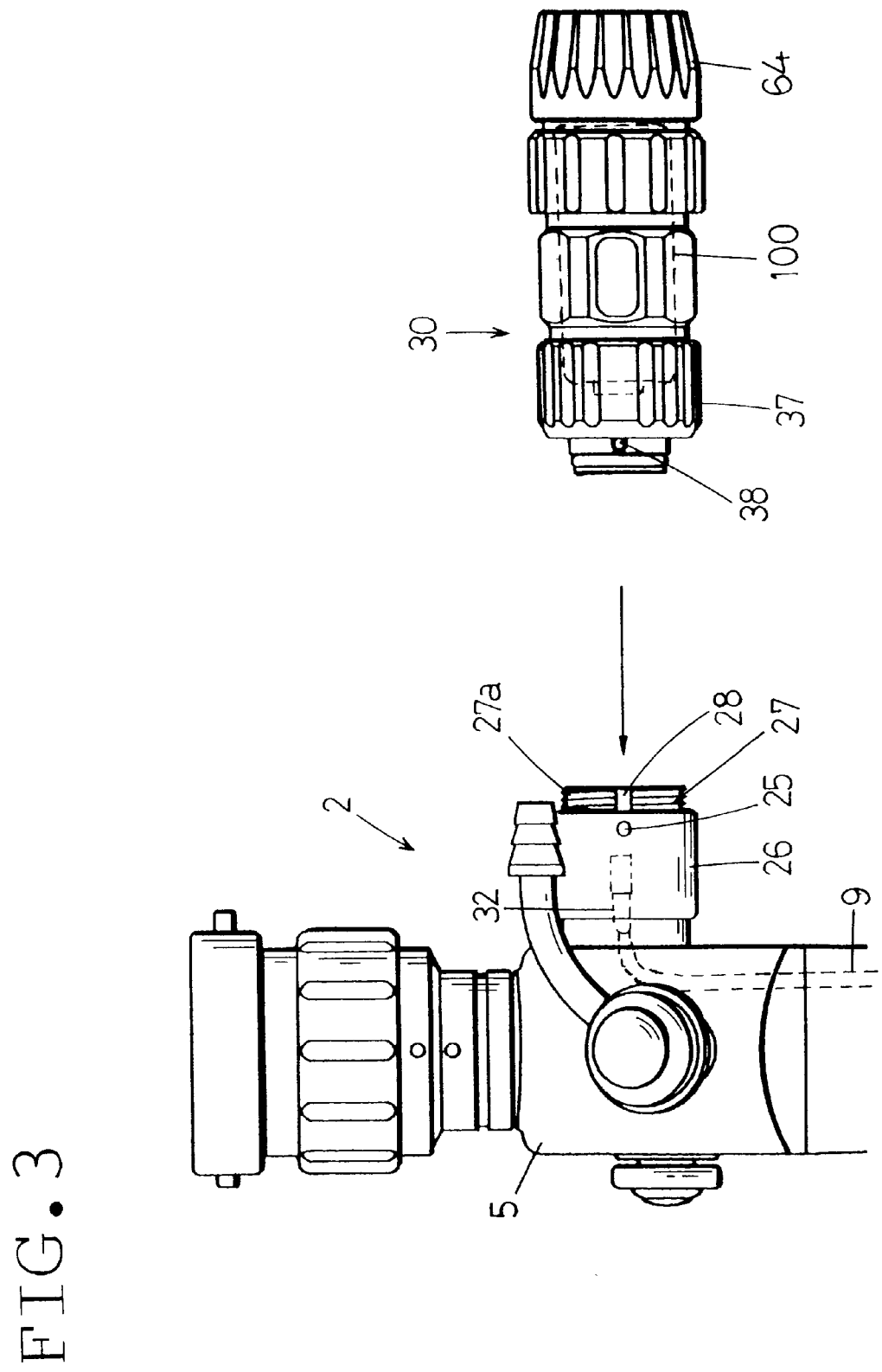
FIG. 3 is a fragmentary front view of the embodiment of the present invention in a state where an illuminating light supply unit is detached from a control part of the endoscope.

FIG. 3 shows the illuminating light supply unit 30 as detached from the control part 2. A unit-connecting socket 27 projects from the control part 2 as described later. The unit-connecting socket 27 has an external thread 27a formed on a projecting end portion thereof. A plastic cover cylinder 26 is provided to surround the unit-connecting socket 27.

The illuminating light supply unit 30 is provided with a fastening ring 37. The fastening ring 37 is rotatable about its own axis and has an internal thread formed on an inner surface thereof. The internal thread is engageable with the external thread 27a provided on the control part 2.

In addition, the illuminating light supply unit 30 is provided with a positioning pin 38 fittable into a regulating groove 28 formed in the projecting end portion of the unit-connecting socket 27. The positioning pin 38 regulates the orientation of the illuminating light supply unit 30 with respect to the control part 2 when the illuminating light supply unit 30 is connected thereto. Reference numeral 25 denotes an index mark for alignment.

As shown in FIG. 3, when the illuminating light supply unit 30 is detached from the control part 2, the battery 100 is within the illuminating light supply unit 30, and the switch control ring 64 is also situated on the illuminating light supply unit 30. However, the light source lamp 32 is left in the control part 2.

Figure 4:
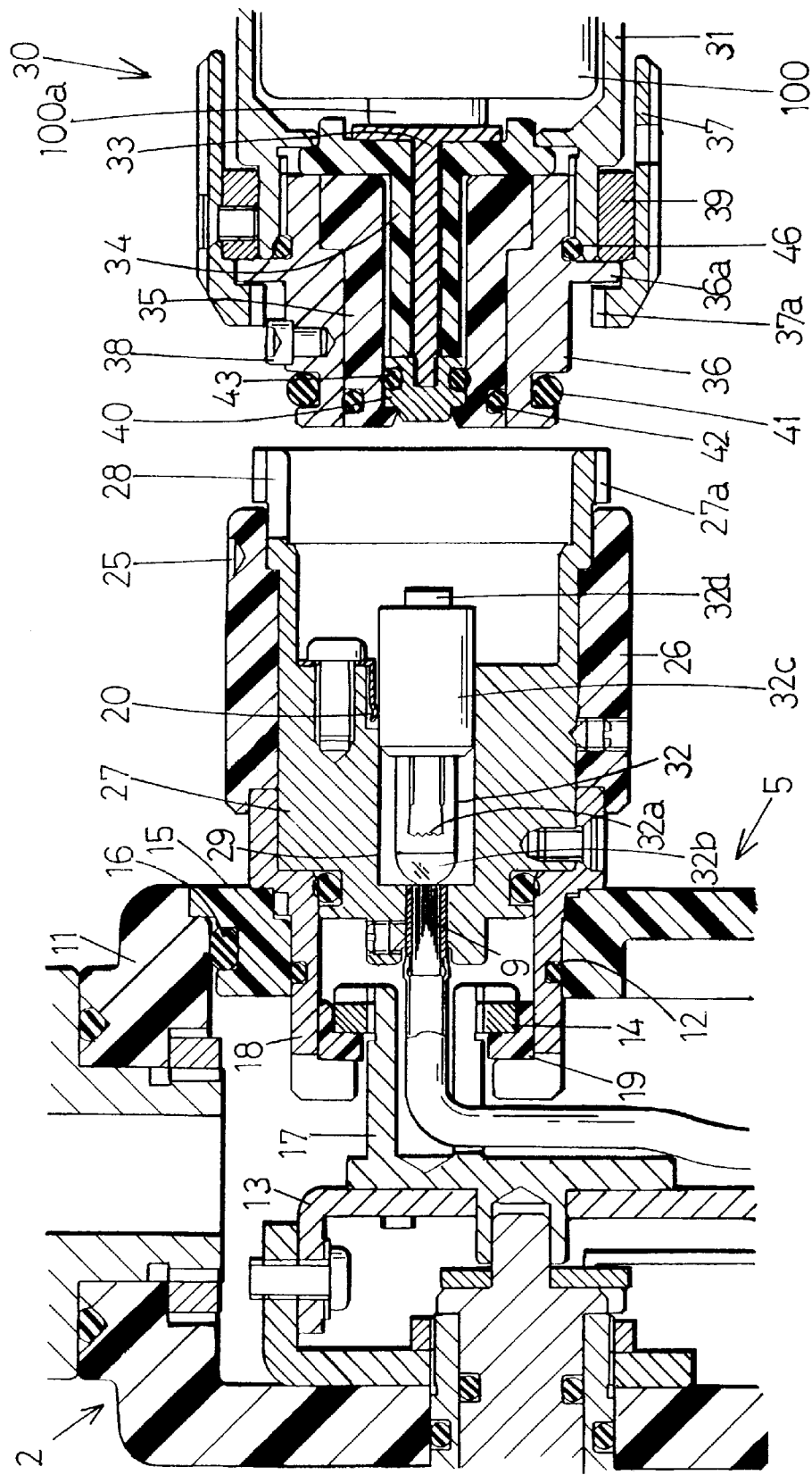
FIG. 4 is a sectional view of the embodiment of the present invention, showing a joint between the endoscope control part and the illuminating light supply unit as detached from the control part.
Figure 5:
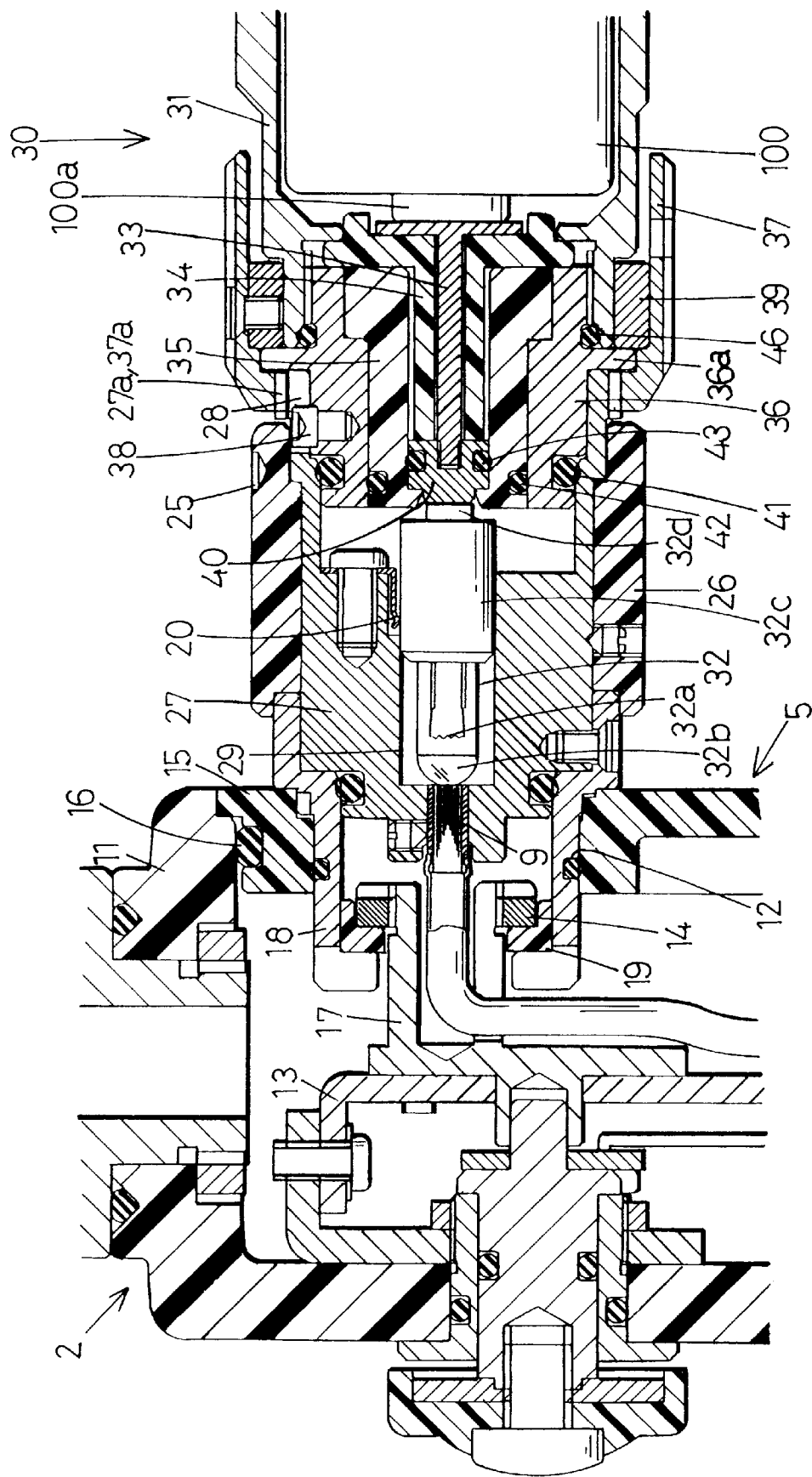
FIG. 5 is a sectional view of the embodiment of the present invention, showing the joint between the endoscope control part and the illuminating light supply unit as connected to the control part.

FIGS. 4 and 5 show the joint between the control part 2 and the illuminating light supply unit 30 and its vicinities. FIG. 4 shows a state where the illuminating light supply unit 30 is detached from the control part 2. FIG. 5 shows a state where the illuminating light supply unit 30 is connected to the control part 2.

The control mechanism portion 5 of the control part 2 is covered with a casing 11 made of an electrically insulating plastic material. A cover 15, which is made of an electrically insulating plastic material, is fitted in a relatively large opening provided in a side of the casing 11. Reference numeral 16 denotes an O-ring for watertight sealing.

A support cylinder 17 is disposed on the central axis of a through-hole formed in the center of the cover 15. The proximal end portion of the support cylinder 17 is secured to a metal frame 13 in the control part 2. A connecting socket receptacle 18 is secured to the cover 15 under pressure by tightening a nut 14 engaged with the head of the support cylinder 17.

It should be noted that an insulating washer 19 made of an electrically insulating plastic material is interposed between the connecting socket receptacle 18 and the nut 14 to prevent contact therebetween. Reference numeral 12 denotes an O-ring for watertight sealing.

The connecting socket receptacle 18 opens to a considerable extent on the outer surface of the cover 15. The proximal portion of the unit-connecting socket 27 is fitted into and screwed to the connecting socket receptacle 18 such that the socket 27 projects outwardly in a cylindrical shape to receive (connect) the illuminating light supply unit 30. The unit-connecting socket 27 is made of a stainless steel, for example. The cover cylinder 26 covers the outer peripheral surfaces of the unit-connecting socket 27 and the connecting socket receptacle 18. The cover cylinder 26 is made of a plastic material of low thermal conductivity.

The entrance end portion of the light guide fiber bundle 9 is secured with a screw at the central axis position on the bottom of the unit-connecting socket 27. The entrance end portion of the light guide fiber bundle 9 faces outwardly in the unit-connecting socket 27. The light source lamp 32 is placed to face the entrance end surface of the light guide fiber bundle 9.

The light source lamp 32 is a miniature bulb with a filament 32a that emits light by being supplied with an electric current. A convex lens 32b is integrally formed at the distal end of the light source lamp 32 to converge light. That is, the light source lamp 32 is a lensed miniature bulb.

The light source lamp 32 is removably fitted into a lamp-receiving bore 29 formed in the axis position on the bottom of the unit-connecting socket 27. The convex lens 32b at the distal end of the light source lamp 32 is placed in direct contact with the entrance end surface of the light guide fiber bundle 9. The optical axis of the convex lens 32b perpendicularly intersects the entrance end surface of the light guide fiber bundle 9.

The outer peripheral surface of a proximal half of the light source lamp 32 serves as a minus electrode 32c. The minus electrode 32c is pressed from a side thereof by a contact spring 20 screwed to the unit-connecting socket 27. In this way, the light source lamp 32 is resiliently secured to the unit-connecting socket 27.

The illuminating light supply unit 30 is formed as a single independent unit whose front and rear end portions are joined by a cylindrical battery chamber casing 31 accommodating the battery 100. The battery chamber casing 31 has a plug 36 thread-engaged with the forward end thereof. When the illuminating light supply unit 30 is connected to the control part 2, the plug 36 is fitted into the mouth of the unit-connecting socket 27.

An O-ring 41 for watertight sealing is fitted on the outer peripheral surface of the plug 36 to come in close contact with the inner peripheral surface of the unit-connecting socket 27. The positioning pin 38 is also provided on the outer peripheral surface of the plug 36. It should be noted that in FIGS. 4 and 5 the positioning pin 38, the index mark 25, etc. are shown as viewed from a direction different from that in FIG. 3 for the sake of illustration.

An electrode member 40 is fixedly disposed in the distal end portion of the plug 36 through an insulating cylinder 35. The electrode member 40 is adapted to come in contact with a plus electrode 32d of the light source lamp 32. An electrode rod 33 contacts a plus electrode 100a of the battery 100. The forward end of the electrode rod 33 is screwed into the electrode member 40. Thus, the electrode member 40 and the electrode rod 33 are electrically and mechanically connected to each other. Reference numeral 34 denotes an electrically insulating material.

In addition, O-rings 42, 43 and 46 for watertight sealing are fitted in the boundaries between the above-described parts that lead to the outer surfaces to prevent water from externally entering the illuminating light supply unit 30.

The fastening ring 37 has a distal end portion with a slightly smaller inner diameter than that of the other portion thereof. The distal end portion of the fastening ring 37 is provided with an internal thread 37a that is engageable with the external thread 27a of the unit-connecting socket 27.

An annular member 39 is screwed to the inner peripheral surface of an intermediate portion of the fastening ring 37. The annular member 39 is rotatably fitted on the outer peripheral surface of the battery chamber casing 31. A collar 36a provided on the plug 36 is loosely held between the annular member 39 and the internal thread 37a.

Accordingly, the fastening ring 37 is almost immovable in the axial direction. However, the fastening ring 37 is rotatable about its own axis. Thus, by rotating the fastening ring 37, the internal thread 37a formed on the distal end portion thereof can be engaged with or disengaged from the external thread 27a of the unit-connecting socket 27.

Accordingly, the plug 36 at the forward end of the illuminating light supply unit 30 is inserted into the unit-connecting socket 27, and the plug 36 and the unit-connecting socket 27 are aligned with each other in terms of their positions in the direction of rotation so that the positioning pin 38 is fitted into the regulating groove 28. In this state, the fastening ring 37 is rotated to engage the internal thread 37a of the fastening ring 37 with the external thread 27a of the unit-connecting socket 27. Consequently, the illuminating light supply unit 30 is connected to the control part 2 as shown in FIG. 5.

Thus, when the illuminating light supply unit 30 is connected to the control part 2, the plus electrode 32d of the light source lamp 32 and the plus electrode 100a of the battery 100 are electrically connected to each other at all times. Therefore, the light source lamp 32 can be turned on by rotating the switch control ring 64. The part containing the light source lamp 32 is sealed with the O-ring 41 in a watertight manner so that water will not externally enter this part.

Illuminating light emitted from the light source lamp 32 is converged by the convex lens 32b to enter the entrance end surface of the light guide fiber bundle 9. The convex lens 32b at the distal end of the light source lamp 32 is placed in close contact with the entrance end surface of the light guide fiber bundle 9. Therefore, a light beam emitted from the filament 32a enters the light guide fiber bundle 9 with a minimum loss of the light quantity due to divergence.

If the fastening ring 37 is rotated to disengage from the unit-connecting socket 27 in a state where the illuminating light supply unit 30 is connected to the control part 2, the illuminating light supply unit 30 can be detached from the control part 2, as shown in FIG. 4.

At this time, the illuminating light supply unit 30, which contains the battery 100, is detached as one unit from the control part 2. However, the light source lamp 32 is left in the lamp-receiving bore 29 of the unit-connecting socket 27.

Accordingly, detaching the illuminating light supply unit 30 from the control part 2 stops the light source lamp 32 from being supplied with electric power from the battery 100 and surely brings the light source lamp 32 into an off-state, regardless of whether the light source lamp 32 has been on or off. When the illuminating light supply unit 30 is detached from the control part 2, the light source lamp 32 can be removed from the lamp-receiving bore 29 for replacement.

Figure 6:
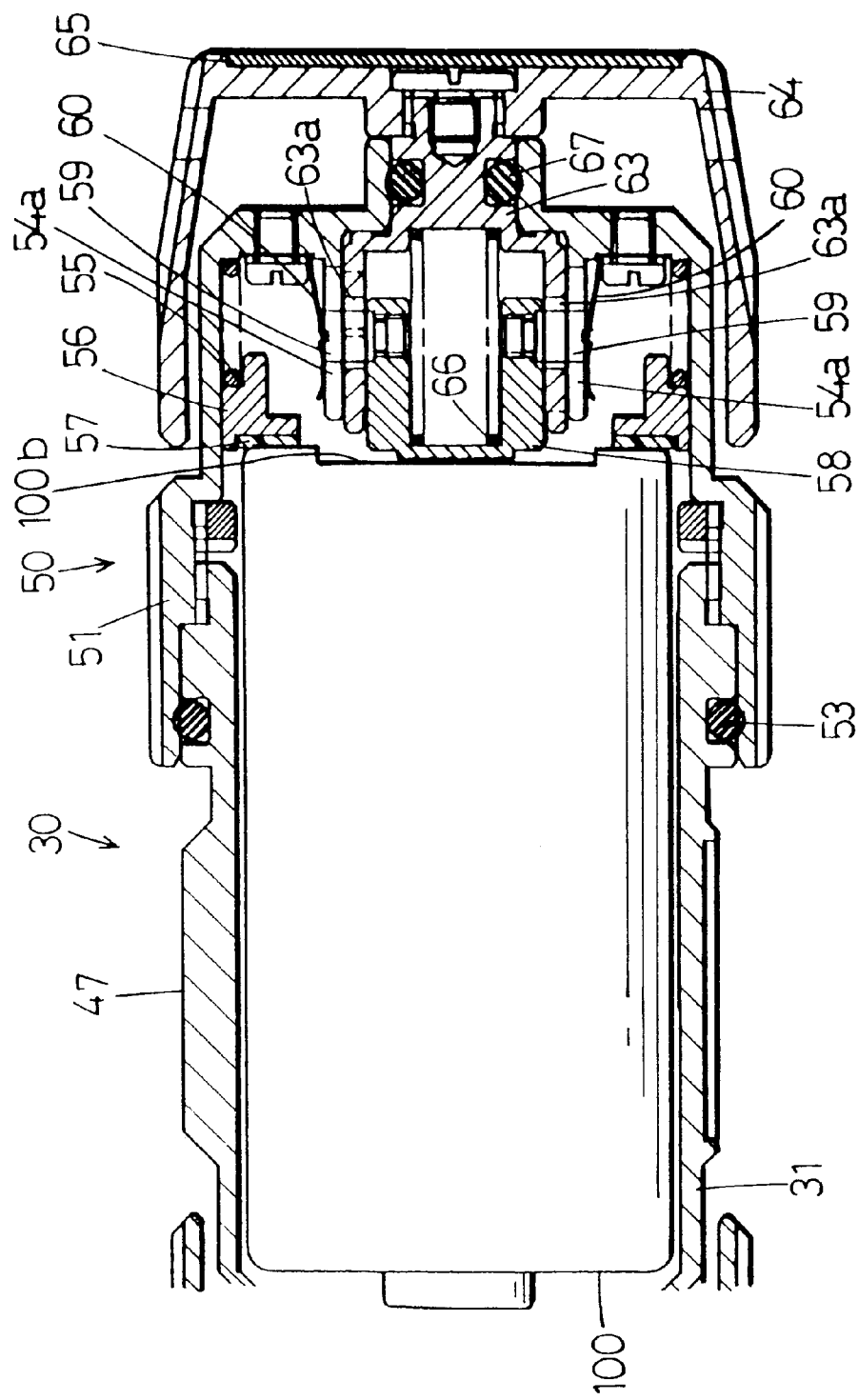
FIG. 6 is a sectional view showing a battery-accommodating portion and terminating end portion of the illuminating light supply unit in the embodiment of the present invention.

FIG. 6 shows the battery-accommodating portion of the illuminating light supply unit 30, together with a terminating end portion thereof. A cap 50 is detachably engaged with an end portion of the battery chamber casing 31, which accommodates the battery 100. The cap 50 incorporates a switch for on/off controlling the supply of electric power from the battery 100 to the light source lamp 32.

A cap body 51 is made of a metallic material of good electrical conductivity. A sealing O-ring 53 is disposed in the area of fit between the outer peripheral surface of the end portion of the battery chamber casing 31 and the inner peripheral surface of the cap body 51, thereby preventing water from entering the inside of the cap 50 through the area of fit therebetween.

A first compression coil spring 55 is retained at one end thereof by the cap body 51 to urge the battery 100 toward the inner side (leftward as viewed in FIG. 6) through an axially movable retaining ring 56, thereby ensuring the contact between the plus electrode 100a of the battery 100 and the electrode rod 33.

The first compression coil spring 55 is disposed in coaxial relation to the battery 100. The retaining ring 56 abuts on the peripheral edge of the battery 100 so as not to contact the minus electrode 100b of the battery 100. Reference numeral 57 denotes a ring-shaped washer of good slip properties.

A rotating cam cylinder 63 is fitted in the cap body 51 so as to be rotatable about the axis of the cap 50. The switch control ring 64 is integrally connected by thread engagement and bonding to the head portion of the rotating cam cylinder 63, which projects to the projecting end side of the cap 50. The switch control ring 64 has a substantially bowl-like configuration and is disposed so as to surround the end portion of the cap 50. Reference numeral 65 denotes a decorative plate.

The head portion of the rotating cam cylinder 63 is rotatably fitted to the inner peripheral surface of the end portion of the cap body 51. A sealing O-ring 67 is provided in the area of fit between the head portion of the rotating cam cylinder 63 and the inner peripheral surface of the cap body 51, thereby preventing water from entering the inside of the illuminating light supply unit 30. Thus, the illuminating light supply unit 30 is formed into a watertight structure that prevents water from externally entering the inside of the illuminating light supply unit 30 through any portion thereof.

A movable contact member 58 contacts the minus electrode 100b of the battery 100. The movable contact member 58 is formed in the shape of a cylinder, one end of which is closed, from a rigid metallic material of good electrical conductivity. The movable contact member 58 is fitted in the rotating cam cylinder 63 so as to be able to axially project from and withdraw into the rotating cam cylinder 63.

The movable contact member 58 has a contact formed on the bottom thereof. The movable contact member 58 is urged by a second compression coil spring 66 to press the contact against the central portion of the minus electrode 100b of the battery 100.

A pair of guide pins 59 of good electrical conductivity project from the outer peripheral surface of the movable contact member 58. The guide pins 59 extend through cam grooves 63a formed in the rotating cam cylinder 63 and are engaged with axially elongated grooves 54a formed in the cap body 51.

Accordingly, the movable contact member 58 is prevented from rotating about its own axis by the engagement between the guide pins 59 and the elongated grooves 54a. When the switch control ring 64 is rotated, the rotating cam cylinder 63 rotates about the axis together with the switch control ring 64. Consequently, the guide pins 59, which are integrated with the movable contact member 58, are axially displaced by the cam grooves 63a, causing the movable contact member 58 to switch between an on-position where it contacts the minus electrode 100b of the battery 100 and an off-position where it is separate from the minus electrode 100b.

Leaf springs 60 abut on the respective tops of the guide pins 59 to ensure the electrical conduction between the guide pins 59 and the cap body 51. In a switch-on state, the minus electrode 100b of the battery 100 is electrically connected to the minus electrode 32c of the light source lamp 32 through the movable contact member 58, the guide pins 59, the leaf springs 60, the cap body 51, the battery chamber casing 31, the plug 36, the unit-connecting socket 27 and the contact spring 20.

When the battery 100 has run down, the cap body 51 is rotated about its own axis. By doing so, the whole cap 50 is detached from the illuminating light supply unit 30. Therefore, the battery 100 can be replaced easily. It should be noted that a coarse knurled portion 47 is formed rather thick on the battery chamber casing 31 so that the battery chamber casing 31 is easy to hold when rotating the cap body 51.

According to the present invention, when the illuminating light supply unit is detached from the control part, the light source lamp is left in the control part. Therefore, when the illuminating light supply unit is detached from the control part, the light source lamp is surely turned off without the need to provide a switch that performs a switching operation in response to attaching and detaching the illuminating light supply unit with respect to the control part, thereby enabling prevention of useless consumption of the power supply.

While the invention has been described by reference to a specific embodiment chosen for purposes of illustration, it should be apparent that numerous modifications could be made thereto by those skilled in the art without departing from the basic concept and scope of the invention.

We claim:

1. A portable endoscope having a light guide for transmitting illuminating light to illuminate an object, said light guide having an entrance portion disposed in a control part of said portable endoscope, said control part having a control mechanism, a grip portion, and an eyepiece, said portable endoscope further having an illuminating light supply unit containing a power supply for supplying the illuminating light to said light guide, said illuminating light supply unit being detachably connected to said control part, said portable endoscope comprising:

a lamp serving as a light source of said illuminating light, said lamp being provided such that when said illuminating light supply unit is detached from said control part, said lamp remains in said control part, wherein said control part has a lamp-receiving bore formed in a portion to which said illuminating light supply unit is detachably connected, said lamp-receiving bore being removably fitted with said lamp, said lamp being resiliently secured in said lamp-receiving bore by a contract spring.

2. A portable endoscope according to claim 1, wherein said power supply is a battery, said battery being contained in said illuminating light supply unit when said illuminating light supply unit is detached from said control part.

3. A portable endoscope according to claim 1, wherein said illuminating light supply unit is provided with a hand-operated switch to turn on and off said lamp, said hand-operated switch being situated on said illuminating light supply unit when said illuminating light supply unit is detached from said control part.

4. A portable endoscope according to claim 1, wherein said lamp can be removed from said lamp-receiving bore for replacement by detaching said illuminating light supply unit from said control part.

5. A portable endoscope according to claim 1, further comprising:

seal means for sealing a portion containing said lamp in a watertight manner so that water will not externally enter said portion when said illuminating light supply unit is detachably connected to said control part, said seal means being provided at a joint between said control part and said illuminating light supply unit.

6. A portable endoscope according to claim 1, wherein said lamp is a light bulb having a lens formed at a distal end thereof, said lamp being provided such that a distal end surface of said lens is placed in close contact with an entrance end surface of said light guide.

7. A portable endoscope, comprising:

a light guide for transmitting illuminating light to illuminate an object, said light guide having an entrance portion disposed in a control part of said portable endoscope, said control part having:
a control mechanism;
a grip portion; and
an eyepiece;

an illuminating light supply unit containing a power supply for supplying power to illuminate said light guide, said illuminating light supply unit being detachably connected to said control part;

a lamp serving as a light source of said illuminating light, said lamp being provided such that when said illuminating light supply unit is detached from said control part, said lamp remains in said control part, wherein said control part has a lamp-receiving bore formed in a portion to which said illuminating light supply unit is detachably connected, said lamp-receiving bore being removably fitted with said lamp, said lamp being resiliently secured in said lamp-receiving bore by a contract spring.

8. A portable endoscope according to claim 7, wherein said power supply comprises a battery, said battery being contained in said illuminating light supply unit when said illuminating light supply unit is detached from said control part.

9. A portable endoscope according to claim 7, wherein said illuminating light supply unit is provided with a hand-operated switch to turn said lamp ON and OFF, said hand-operated switch being situated on said illuminating light supply unit when said illuminating light supply unit is detached from said control part.

10. A portable endoscope according to claim 7, said lamp being removable from said lamp-receiving bore by detachment of said illuminating light supply unit from said control part.

11. A portable endoscope according to claim 7, further comprising:

a seal that seals a portion containing said lamp in a watertight manner so that water will not enter said portion when said illuminating light supply unit is detachably connected to said control part, said seal means being provided at a joint between said control part and said illuminating light supply unit.

12. A portable endoscope according to claim 7, wherein said lamp comprises a light bulb having a lens formed at a distal end such that a distal end surface of said lens is placed in close contact with an entrance end surface of said light guide.

* * * * *